United States Patent
Kanbara et al.

(10) Patent No.: US 8,993,774 B2
(45) Date of Patent: Mar. 31, 2015

(54) PROCESS FOR PRODUCTION OF AROMATIC ALCOHOL OR HETEROCYCLIC AROMATIC ALCOHOL

(75) Inventors: Yutaka Kanbara, Niigata (JP); Takafumi Abe, Niigata (JP); Norio Fushimi, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/996,759

(22) PCT Filed: Dec. 22, 2011

(86) PCT No.: PCT/JP2011/079924
§ 371 (c)(1), (2), (4) Date: Jul. 9, 2013

(87) PCT Pub. No.: WO2012/086808
PCT Pub. Date: Jun. 28, 2012

(65) Prior Publication Data
US 2013/0303775 A1 Nov. 14, 2013

(30) Foreign Application Priority Data

Dec. 24, 2010 (JP) ................................. 2010-288352
Oct. 28, 2011 (JP) ................................. 2011-237443

(51) Int. Cl.
| | |
|---|---|
| C07D 211/70 | (2006.01) |
| C07B 41/02 | (2006.01) |
| C07C 29/00 | (2006.01) |
| C07C 41/26 | (2006.01) |
| C07C 29/128 | (2006.01) |
| C07D 213/30 | (2006.01) |
| C07C 213/00 | (2006.01) |
| C07C 29/09 | (2006.01) |
| B01J 23/04 | (2006.01) |

(52) U.S. Cl.
CPC ................. *C07B 41/02* (2013.01); *C07C 29/00* (2013.01); *B01J 23/04* (2013.01); *C07C 41/26* (2013.01); *C07C 29/128* (2013.01); *C07D 213/30* (2013.01); *C07C 213/00* (2013.01); *C07C 29/09* (2013.01)
USPC .......................................................... 546/344

(58) Field of Classification Search
None
See application file for complete search history.

(56) References Cited

U.S. PATENT DOCUMENTS 4,507,510 A    3/1985    Yoshinaka et al.

FOREIGN PATENT DOCUMENTS

| JP | 59 157039 | 9/1984 |
| JP | 59 163332 | 9/1984 |
| JP | 5 279282 | 10/1993 |
| JP | 6 9458 | 1/1994 |
| JP | 2000 302709 | 10/2000 |

OTHER PUBLICATIONS

Deka, D.C. et al., "Acid Catalysed Pressure Synthesis of N-Ethylbenzylamine from Benzylamine and Ethanol", Journal of Chemical Technology and Biotechnology, Society of Chemical Industry, vol. 41, pp. 95 to 104, (1988).
International Search Report Issued Mar. 19, 2012 in PCT/JP11/79924 Filed Dec. 22, 2011.

*Primary Examiner* — Heidi Reese
(74) *Attorney, Agent, or Firm* — Oblon, McClelland, Maier & Neustadt, L.L.P.

(57) ABSTRACT

A process of production of an aromatic alcohol or a heterocyclic aromatic alcohol, containing a step of reacting an aromatic amine or a heterocyclic aromatic amine having an aromatic ring or a heterocyclic aromatic ring having thereon at least one substituent —$CHR^1NR^2R^3$ (wherein $R^1$, $R^2$ and $R^3$ each independently represent hydrogen, an alkyl group having from 1 to 4 carbon atoms, or a benzyl group), with an alcohol, in the presence of a basic catalyst.

15 Claims, No Drawings

PROCESS FOR PRODUCTION OF AROMATIC ALCOHOL OR HETEROCYCLIC AROMATIC ALCOHOL

TECHNICAL FIELD

The present invention relates to a process for production of an aromatic alcohol or a heterocyclic aromatic alcohol.

BACKGROUND ART

An aromatic alcohol and a heterocyclic aromatic alcohol may be used as a raw material of a medical drug, agrichemicals and the like, or a plasticizer and a paint solvent, and thus are useful in organic synthetic chemistry. An aromatic polyhydric alcohol and a heterocyclic aromatic polyhydric alcohol are important compounds as a raw material of a polymer substance, such as a synthetic fiber and a synthetic resin, for example, polyester and polyurethane.

The following processes have been known as an industrial production process of an aromatic alcohol. Patent Document 1 discloses a process of catalytic hydrogenation of an aromatic carboxylate ester, Patent Document 2 discloses a process of hydrolysis of benzyl chloride, and Patent Document 3 discloses a process of diazotizing benzylamine through reaction with a nitrite salt and then decomposing.

However, these processes have the following problems and thus are not always suitable for industrial production. Specifically, the process disclosed in Patent Document 1 requires a high temperature and a high pressure, and thus the target alcohol tends to be further reduced to form an aromatic hydrocarbon as a by-product. The process disclosed in Patent Document 2 uses chlorine, which brings about problems of corrosion of equipments and treatment of salts. The process disclosed in Patent Document 3 requires a nitrite salt, which is expensive, as a raw material, and furthermore has a problem in treatment of salts.

An industrially useful process of production of a heterocyclic aromatic alcohol has not yet been known.

PRIOR ART DOCUMENT

Patent Documents

Patent Document 1: JP-A-5-279282
Patent Document 2: JP-A-6-9458
Patent Document 3: JP-A-59-157039

SUMMARY OF THE INVENTION

Problems to be Solved by the Invention

An object of the present invention is to provide a process of production of an aromatic alcohol and a heterocyclic aromatic alcohol industrially with high efficiency.

Means for Solving the Problems

The present inventors have found that an aromatic alcohol or a heterocyclic aromatic alcohol may be easily produced by reacting an aromatic amine or a heterocyclic aromatic amine with an alcohol in the presence of a basic catalyst, and thus the present invention has been completed.

The present invention provides a process of production of an aromatic alcohol or a heterocyclic aromatic alcohol, containing a step of reacting an aromatic amine or a heterocyclic aromatic amine having an aromatic ring or a heterocyclic aromatic ring having thereon at least one substituent —$CHR^1NR^2R^3$ (wherein $R^1$, $R^2$ and $R^3$ each independently represent hydrogen, an alkyl group having from 1 to 4 carbon atoms, or a benzyl group), with an alcohol, in the presence of a basic catalyst.

Advantages of the Invention

According to the production process of the present invention, an aromatic alcohol and a heterocyclic aromatic alcohol may be produced with high efficiency from inexpensive raw materials, and thus the process is significantly useful in industry.

EMBODIMENTS FOR CARRYING OUT THE INVENTION

The present invention relates to a process of production of an aromatic alcohol or a heterocyclic aromatic alcohol, containing a step of reacting an aromatic amine or a heterocyclic aromatic amine having an aromatic ring or a heterocyclic aromatic ring having thereon at least one substituent —$CHR^1NR^2R^3$ (wherein $R^1$, $R^2$ and $R^3$ each independently represent hydrogen, an alkyl group having from 1 to 4 carbon atoms, or a benzyl group), with an alcohol, in the presence of a basic catalyst. Aromatic amines and heterocyclic aromatic amines represented by the following formulae (1) to (4) are preferred:

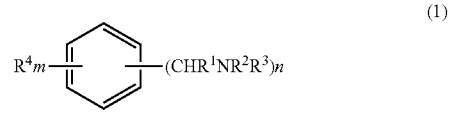

(1)

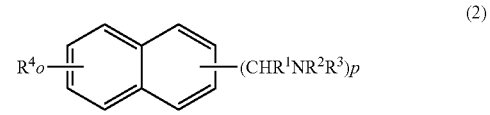

(2)

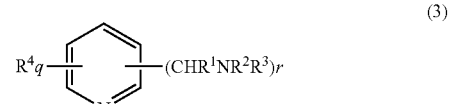

(3)

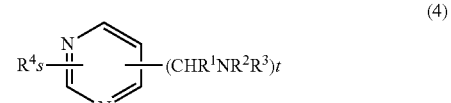

(4)

wherein $R^1$, $R^2$ and $R^3$ each independently represent hydrogen, an alkyl group having from 1 to 4 carbon atoms, or a benzyl group; $R^4$ is selected from an alkyl group having from 1 to 10 carbon atoms, a cycloalkyl group having from 3 to 8 carbon atoms, an alkoxy group having from 1 to 10 carbon atoms, a phenyl group, a benzyl group, a hydroxyl group, a cyano group, an amide group and a halogen atom; m represents an integer of from 0 to 5; n represents an integer of from 1 to 4; o represents an integer of from 0 to 7; p represents an integer of from 1 to 4; q represents an integer of from 0 to 4; r represents an integer of from 1 to 3; s represents an integer of from 0 to 3; and t represents an integer of from 1 to 2, provided that m+n is from 1 to 6, o+p is from 1 to 8, q+r is from 1 to 5, and s+t is from 1 to 4.

Among the aromatic amines and the heterocyclic aromatic amines represented by the aforementioned general formulae, representative examples thereof include compounds represented by the following formulae (5) to (7):

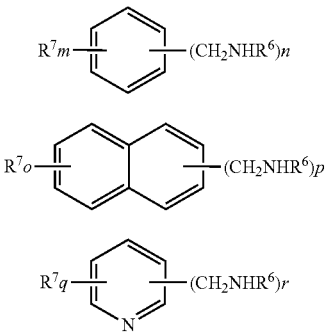

wherein $R^6$ represents hydrogen or an alkyl group having from 1 to 4 carbon atoms; $R^7$ is selected from an alkyl group having from 1 to 10 carbon atoms, a cycloalkyl group having from 3 to 8 carbon atoms, an alkoxy group having from 1 to 10 carbon atoms, a phenyl group, a benzyl group, a hydroxyl group, a cyano group, an amide group and a halogen atom; m represents an integer of from 0 to 5; n represents an integer of from 1 to 4; o represents an integer of from 0 to 7; p represents an integer of from 1 to 4; q represents an integer of from 0 to 4; and r represents an integer of from 1 to 3, provided that m+n is from 1 to 6, o+p is from 1 to 8, and q+r is from 1 to 5.

The reaction of the aromatic amine or the heterocyclic aromatic amine with an alcohol is expressed, for example, by the following reaction schemes (8) and (9):

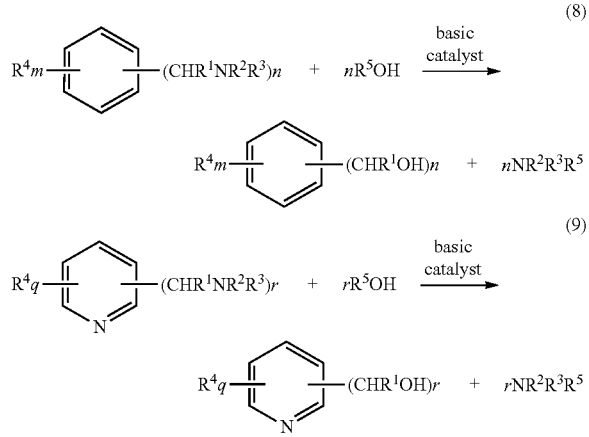

wherein $R^1$ to $R^4$, m, n, q and r have the same meanings as above; and $R^5$ represents a linear or branched alkyl group or a cycloalkyl group each having from 1 to 11 carbon atoms, or an alkyl group having from 1 to 3 carbon atoms having a phenyl group substituted thereon.

In the production process of the present invention, an aromatic alcohol or a heterocyclic aromatic alcohol having an aromatic ring or a heterocyclic aromatic ring having thereon at least one substituent —$CHR^1OH$ (wherein $R^1$ has the same meaning as above) is formed. As apparent from the reaction schemes, an alkyl amine formed by substituting the hydroxyl group of the raw material alcohol with an amino group is simultaneously formed.

The aromatic amine used in the production process of the present invention is not particularly limited as far as the aromatic amine has an aromatic ring having thereon at least one substituent —$CHR^1NR^2R^3$ (wherein $R^1$, $R^2$ and $R^3$ have the same meanings as above).

Examples of the aromatic amine that has a benzene ring as the aromatic ring thereof include benzylamine and secondary and tertiary amines obtained by substituting hydrogen of the aminomethyl group thereof with an alkyl group, a poly(aminomethyl)benzene having a benzene ring and plural amino methyl groups connected thereto and secondary and tertiary amines obtained by substituting hydrogen of the aminomethyl group thereof with an alkyl group, and a substituted benzylamine formed by substituting hydrogen of the benzene ring. Examples of the substituent on the benzene ring include an alkyl group having from 1 to 10 carbon atoms, such as a methyl group, an ethyl group, a propyl group, a butyl group, a pentyl group, a hexyl group, a heptyl group, an octyl group, a nonyl group and a decyl group, which may be linear or branched, a cyclohexyl group, a phenyl group and a benzyl group; an alkoxy group having from 1 to 10 carbon atoms, such as a methoxy group, an ethoxy group, a propoxy group and a butoxy group, which may be linear or branched, and a phenoxy group; a hydroxyl group; a cyano group; an amide group; an amino group; and a halogen atom, such as a chlorine atom, a fluorine atom and a bromine atom.

Specific examples thereof include benzylamine, dibenzylamine, o-xylylenediamine, m-xylylenediamine, p-xylylenediamine, 1,3,5-tri(aminomethyl)benzene, 1,2,4-tri(aminomethyl)benzene, 1,2,4,5-tetra(aminomethylbenzene), N-methylbenzylamine, N-ethylbenzylamine, N-propylbenzylamine, N-butylbenzylamine, 2-methylbenzylamine, 3-methylbenzylamine, 4-methylbenzylamine, 2-ethylbenzylamine, 3-ethylbenzylamine, 4-ethylbenzylamine, 2-propylbenzylamine, 3-propylbenzylamine, 4-propylbenzylamine, 2-butylbenzylamine, 3-butylbenzylamine, 4-butylbenzylamine, 2-pentylbenzylamine, 3-pentylbenzylamine, 4-pentylbenzylamine, 2-hexylbenzylamine, 3-hexylbenzylamine, 4-hexylbenzylamine, 2-heptylbenzylamine, 3-heptylbenzylamine, 4-heptylbenzylamine, 2-octylbenzylamine, 3-octylbenzylamine, 4-octylbenzylamine, 2-nonylbenzylamine, 3-nonylbenzylamine, 4-nonylbenzylamine, 2-decylbenzylamine, 3-decylbenzylamine, 4-decylbenzylamine, 2-cyclohexylbenzylamine, 3-cyclohexylbenzylamine, 4-cyclohexylbenzylamine, 2-phenylbenzylamine, 3-phenylbenzylamine, 4-phenylbenzylamine, 2-benzylbenzylamine, 3-benzylbenzylamine, 4-benzylbenzylamine, 1-phenylethylamine, 2-chlorobenzylamine, 3-chlorobenzylamine, 4-chlorobenzylamine, 2-fluorobenzylamine, 3-fluorobenzylamine, 4-fluorobenzylamine, 2-iodobenzylamine, 3-iodobenzylamine, 4-iodobenzylamine, 2-methoxybenzylamine, 3-methoxybenzylamine, 4-methoxybenzylamine, 2-ethoxybenzylamine, 3-ethoxybenzylamine, 4-ethoxybenzylamine, 2-propoxybenzylamine, 3-propoxybenzylamine, 4-propoxybenzylamine, 2-butoxybenzylamine, 3-butoxybenzylamine, 4-butoxybenzylamine, 2-phenoxybenzylamine, 3-phenoxybenzylamine, 4-phenoxybenzylamine, 2-hydroxybenzylamine, 3-hydroxybenzylamine, 4-hydroxybenzylamine, 2-cyanobenzylamine, 3-cyanobenzylamine, 4-cyanobenzylamine, 2-(aminomethyl)benzamide, 3-(aminomethyl)benzamide, 4-(aminomethyl)benzamide, aminobenzylamine and (dimethylamino)benzylamine. The aromatic amines may be used solely or as a combination of two or more kinds thereof. Among these, m-xylylenediamine and p-xylylenediamine are useful from the standpoint of the use of the resulting aromatic alcohol as a polymer raw material.

Xylylenediamine may be produced industrially through ammoxidation and hydrogenation of xylene.

Examples of the aromatic amine that has a naphthalene ring as the aromatic ring thereof include naphthalenemethylamine and secondary and tertiary amines obtained by substituting hydrogen of the aminomethyl group thereof with an alkyl group, a poly(aminomethyl)naphthalene having a naphthalene ring and plural amino methyl groups connected thereto and secondary and tertiary amines obtained by substituting hydrogen of the aminomethyl group thereof with an alkyl group, and a substituted naphthalenemethylamine formed by substituting hydrogen of the naphthalene ring. Examples of the substituent on the naphthalene ring include an alkyl group having from 1 to 10 carbon atoms, such as a methyl group, an ethyl group, a propyl group, a butyl group, a pentyl group, a hexyl group, a heptyl group, an octyl group, a nonyl group and a decyl group, which may be linear or branched; a cyclohexyl group; a phenyl group; a benzyl group; an alkoxy group having from 1 to 10 carbon atoms, such as a methoxy group, an ethoxy group, a propoxy group and a butoxy group, which may be linear or branched; an aryloxy group, such as a phenoxy group; a hydroxyl group; a cyano group; an amide group; an amino group; and a halogen atom, such as a chlorine atom, a fluorine atom and a bromine atom.

Specific examples thereof include 1-naphthalenemethylamine, 2-naphthalenemethylamine, N-methyl-1-naphthalenemethylamine, N-methyl-2-naphthalenemethylamine, 2-methyl-1-naphthalenemethylamine, 3-methyl-1-naphthalenemethylamine, 4-methyl-1-naphthalenemethylamine, 5-methyl-1-naphthalenemethylamine, 6-methyl-1-naphthalenemethylamine, 7-methyl-1-naphthalenemethylamine, 8-methyl-1-naphthalenemethylamine, 1-methyl-2-naphthalenemethylamine, 3-methyl-2-naphthalenemethylamine, 4-methyl-2-naphthalenemethylamine, 5-methyl-2-naphthalenemethylamine, 6-methyl-2-naphthalenemethylamine, 7-methyl-2-naphthalenemethylamine, 8-methyl-2-naphthalenemethylamine, 2-ethyl-1-naphthalenemethylamine, 3-ethyl-1-naphthalenemethylamine, 4-ethyl-1-naphthalenemethylamine, 5-ethyl-1-naphthalenemethylamine, 6-ethyl-1-naphthalenemethylamine, 7-ethyl-1-naphthalenemethylamine, 8-ethyl-1-naphthalenemethylamine, 1-ethyl-2-naphthalenemethylamine, 3-ethyl-2-naphthalenemethylamine, 4-ethyl-2-naphthalenemethylamine, 5-ethyl-2-naphthalenemethylamine, 6-ethyl-2-naphthalenemethylamine, 7-ethyl-2-naphthalenemethylamine, 8-ethyl-2-naphthalenemethylamine, 2-butyl-1-naphthalenemethylamine, 3-butyl-1-naphthalenemethylamine, 4-butyl-1-naphthalenemethylamine, 5-butyl-1-naphthalenemethylamine, 6-butyl-1-naphthalenemethylamine, 7-butyl-1-naphthalenemethylamine, 8-butyl-1-naphthalenemethylamine, 1-butyl-2-naphthalenemethylamine, 3-butyl-2-naphthalenemethylamine, 4-butyl-2-naphthalenemethylamine, 5-butyl-2-naphthalenemethylamine, 6-butyl-2-naphthalenemethylamine, 7-butyl-2-naphthalenemethylamine, 8-butyl-2-naphthalenemethylamine, 2-hexyl-1-naphthalenemethylamine, 3-hexyl-1-naphthalenemethylamine, 4-hexyl-1-naphthalenemethylamine, 5-hexyl-1-naphthalenemethylamine, 6-hexyl-1-naphthalenemethylamine, 7-hexyl-1-naphthalenemethylamine, 8-hexyl-1-naphthalenemethylamine, 1-hexyl-2-naphthalenemethylamine, 3-hexyl-2-naphthalenemethylamine, 4-hexyl-2-naphthalenemethylamine, 5-hexyl-2-naphthalenemethylamine, 6-hexyl-2-naphthalenemethylamine, 7-hexyl-2-naphthalenemethylamine, 8-hexyl-2-naphthalenemethylamine, 2-decyl-1-naphthalenemethylamine, 3-decyl-1-naphthalenemethylamine, 4-decyl-1-naphthalenemethylamine, 5-decyl-1-naphthalenemethylamine, 6-decyl-1-naphthalenemethylamine, 7-decyl-1-naphthalenemethylamine, 8-decyl-1-naphthalenemethylamine, 1-decyl-2-naphthalenemethylamine, 3-decyl-2-naphthalenemethylamine, 4-decyl-2-naphthalenemethylamine, 5-decyl-2-naphthalenemethylamine, 6-decyl-2-naphthalenemethylamine, 7-decyl-2-naphthalenemethylamine, 8-decyl-2-naphthalenemethylamine, 2-cyclohexyl-1-naphthalenemethylamine, 3-cyclohexyl-1-naphthalenemethylamine, 4-cyclohexyl-1-naphthalenemethylamine, 5-cyclohexyl-1-naphthalenemethylamine, 6-cyclohexyl-1-naphthalenemethylamine, 7-cyclohexyl-1-naphthalenemethylamine, 8-cyclohexyl-1-naphthalenemethylamine, 1-cyclohexyl-2-naphthalenemethylamine, 3-cyclohexyl-2-naphthalenemethylamine, 4-cyclohexyl-2-naphthalenemethylamine, 5-cyclohexyl-2-naphthalenemethylamine, 6-cyclohexyl-2-naphthalenemethylamine, 7-cyclohexyl-2-naphthalenemethylamine, 8-cyclohexyl-2-naphthalenemethylamine, 2-phenyl-1-naphthalenemethylamine, 3-phenyl-1-naphthalenemethylamine, 4-phenyl-1-naphthalenemethylamine, 5-phenyl-1-naphthalenemethylamine, 6-phenyl-1-naphthalenemethylamine, 7-phenyl-1-naphthalenemethylamine, 8-phenyl-1-naphthalenemethylamine, 1-phenyl-2-naphthalenemethylamine, 3-phenyl-2-naphthalenemethylamine, 4-phenyl-2-naphthalenemethylamine, 5-phenyl-2-naphthalenemethylamine, 6-phenyl-2-naphthalenemethylamine, 7-phenyl-2-naphthalenemethylamine, 8-phenyl-2-naphthalenemethylamine, 2-benzyl-1-naphthalenemethylamine, 3-benzyl-1-naphthalenemethylamine, 4-benzyl-1-naphthalenemethylamine, 5-benzyl-1-naphthalenemethylamine, 6-benzyl-1-naphthalenemethylamine, 7-benzyl-1-naphthalenemethylamine, 8-benzyl-1-naphthalenemethylamine, 1-benzyl-2-naphthalenemethylamine, 3-benzyl-2-naphthalenemethylamine, 4-benzyl-2-naphthalenemethylamine, 5-benzyl-2-naphthalenemethylamine, 6-benzyl-2-naphthalenemethylamine, 7-benzyl-2-naphthalenemethylamine, 8-benzyl-2-naphthalenemethylamine, 2-methoxy-1-naphthalenemethylamine, 3-methoxy-1- naphthalenemethylamine, 4-methoxy-1-naphthalenemethylamine, 5-methoxy-1-naphthalenemethylamine, 6-methoxy-1-naphthalenemethylamine, 7-methoxy-1-naphthalenemethylamine, 8-methoxy-1-naphthalenemethylamine, 1-methoxy-2-naphthalenemethylamine, 3-methoxy-2-naphthalenemethylamine, 4-methoxy-2-naphthalenemethylamine, 5-methoxy-2-naphthalenemethylamine, 6-methoxy-2-naphthalenemethylamine, 7-methoxy-2-naphthalenemethylamine, 8-methoxy-2-naphthalenemethylamine, 2-ethoxy-1-naphthalenemethylamine, 3-ethoxy-1-naphthalenemethylamine, 4-ethoxy-1-naphthalenemethylamine, 5-ethoxy-1-naphthalenemethylamine, 6-ethoxy-1-naphthalenemethylamine, 7-ethoxy-1-naphthalenemethylamine, 8-ethoxy-1-naphthalenemethylamine, 1-ethoxy-2-naphthalenemethylamine, 3-ethoxy-2-naphthalenemethylamine, 4-ethoxy-2-naphthalenemethylamine, 5-ethoxy-2-naphthalenemethylamine, 6-ethoxy-2-naphthalenemethylamine, 7-ethoxy-2-naphthalenemethylamine, 8-ethoxy-2-naphthalenemethylamine, 2-propoxy-1-naphthalenemethylamine, 3-propoxy-1-naphthalenemethylamine, 4-propoxy-1-naphthalenemethylamine, 5-propoxy-1-naphthalenemethylamine, 6-propoxy-1-naphthalenemethylamine, 7-propoxy-1-naphthalenemethylamine, 8-propoxy-1-naphthalenemethylamine, 1-propoxy-2-naphthalenemethylamine, 3-propoxy-2-naphthalenemethylamine, 4-propoxy-2-naphthalenemethylamine, 5-propoxy-2-naphthalenemethylamine, 6-propoxy-2-naphthalenemethylamine, 7-propoxy-2-naphthalenemethylamine, 8-propoxy-2-naphthalenemethylamine, 2-phenoxy-1-naphthalenemethylamine, 3-phenoxy-1-naphthalenemethylamine, 4-phenoxy-1-naphthalenemethylamine, 5-phenoxy-1-naphthalenemethylamine, 6-phenoxy-1-naphthalenemethylamine, 7-phenoxy-1-naphthalenemethylamine, 8-phenoxy-1-naphthalenemethylamine, 1-phenoxy-2-naphthalenemethylamine, 3-phenoxy-2-naphthalenemethylamine, 4-phenoxy-2-naphthalenemethylamine, 5-phenoxy-2-naphthalenemethylamine, 6-phenoxy-2-naphthalenemethylamine, 7-phenoxy-2-naphthalenemethylamine, 8-phenoxy-2-naphthalenemethylamine, 2-hydroxy-1-naphthalenemethylamine, 3-hydroxy-1-naphthalenemethylamine, 4-hydroxy-1-naphthalenemethylamine, 5-hydroxy-1-naphthalenemethylamine, 6-hydroxy-1-naphthalenemethylamine, 7-hydroxy-1-naphthalenemethylamine, 8-hydroxy-1-naphthalenemethylamine, 1-hydroxy-2-naphthalenemethylamine, 3-hydroxy-2-naphthalenemethylamine, 4-hydroxy-2-naphthalenemethylamine, 5-hydroxy-2-naphthalenemethylamine, 6-hydroxy-2-naphthalenemethylamine, 7-hydroxy-2-naphthalenemethylamine, 8-hydroxy-2-naphthalenemethylamine, 2-cyano-1-naphthalenemethylamine, 3-cyano-1-naphthalenemethylamine, 4-cyano-1-naphthalenemethylamine, 5-cyano-1-naphthalenemethylamine, 6-cyano-1-naphthalenemethylamine, 7-cyano-1-naphthalenemethylamine, 8-cyano-1-naphthalenemethylamine, 1-cyano-2-naphthalenemethylamine, 3-cyano-2-naphthalenemethylamine, 4-cyano-2-naphthalenemethylamine, 5-cyano-2-naphthalenemethylamine, 6-cyano-2-naphthalenemethylamine, 7-cyano-2-naphthalenemethylamine, 8-cyano-2-naphthalenemethylamine, 1-aminomethyl-2-naphthaleneamide, 1-aminomethyl-3-naphthaleneamide, 1-aminomethyl-4-naphthaleneamide, 1-aminomethyl-5-naphthaleneamide, 1-aminomethyl-6-naphthaleneamide, 1-aminomethyl-7-naphthaleneamide, 1-aminomethyl-8-naphthaleneamide, 2-aminomethyl-1-naphthaleneamide, 2-aminomethyl-3-naphthaleneamide, 2-aminomethyl-4-naphthaleneamide, 2-aminomethyl-5-naphthaleneamide, 2-aminomethyl-6-naphthaleneamide, 2-aminomethyl-7-naphthaleneamide, 2-aminomethyl-8-naphthaleneamide, 2-chloro-1-naphthalenemethylamine, 3-chloro-1-naphthalenemethylamine, 4-chloro-1-naphthalenemethylamine, 5-chloro-1-naphthalenemethylamine, 6-chloro-1-naphthalenemethylamine, 7-chloro-1-naphthalenemethylamine, 8-chloro-1-naphthalenemethylamine, 1-chloro-2-naphthalenemethylamine, 3-chloro-2-naphthalenemethylamine, 4-chloro-2-naphthalenemethylamine, 5-chloro-2-naphthalenemethylamine, 6-chloro-2-naphthalenemethylamine, 7-chloro-2-naphthalenemethylamine, 8-chloro-2-naphthalenemethylamine, 2-fluoro-1-naphthalenemethylamine, 3-fluoro-1-naphthalenemethylamine, 4-fluoro-1-naphthalenemethylamine, 5-fluoro-1-naphthalenemethylamine, 6-fluoro-1-naphthalenemethylamine, 7-fluoro-1-naphthalenemethylamine, 8-fluoro-1-naphthalenemethylamine, 1-fluoro-2-naphthalenemethylamine, 3-fluoro-2-naphthalenemethylamine, 4-fluoro-2-naphthalenemethylamine, 5-fluoro-2-naphthalenemethylamine, 6-fluoro-2-naphthalenemethylamine, 7-fluoro-2-naphthalenemethylamine, 8-fluoro-2-naphthalenemethylamine, 2-iodo-1-naphthalenemethylamine, 3-iodo-1-naphthalenemethylamine, 4-iodo-1-naphthalenemethylamine, 5-iodo-1-naphthalenemethylamine, 6-iodo-1-naphthalenemethylamine, 7-iodo-1-naphthalenemethylamine, 8-iodo-1-naphthalenemethylamine, 1-iodo-2-naphthalenemethylamine, 3-iodo-2-naphthalenemethylamine, 4-iodo-2-naphthalenemethylamine, 5-iodo-2-naphthalenemethylamine, 6-iodo-2-naphthalenemethylamine, 7-iodo-2-naphthalenemethylamine and 8-iodo-2-naphthalenemethylamine. The aromatic amines may be used solely or as a combination of two or more kinds thereof.

Examples of the aromatic amine also include a tricyclic amine, such as anthracenemethylamine.

The heterocyclic aromatic amine used in the production process of the present invention is not particularly limited as far as the heterocyclic aromatic amine has a heterocyclic aromatic ring having thereon at least one substituent —$CHR^1NR^2R^3$ (wherein $R^1$, $R^2$ and $R^3$ have the same meanings as above). Examples thereof include (aminomethyl)pyridine, (aminomethyl)pyrimidine, (aminomethyl)pyridine, and secondary and tertiary amines obtained by substituting hydrogen of the aminomethyl group thereof with an alkyl group; a poly(aminomethyl)pyridine and a poly(aminomethyl)pyrimidine having a pyridine ring or a pyrimidine ring and plural aminomethyl groups bonded thereto, and secondary and tertiary amines obtained by substituting hydrogen of the aminomethyl group thereof with an alkyl group; and a substituted (aminomethyl)pyridine and a substituted (aminomethyl)pyrimidine formed by substituting hydrogen of the heterocyclic aromatic ring.

Examples of the substituent on the heterocyclic aromatic group include an alkyl group having from 1 to 10 carbon atoms, such as a methyl group, an ethyl group, a propyl group, a butyl group, a pentyl group, a hexyl group, a heptyl group, an octyl group, a nonyl group and a decyl group, which may be linear or branched; a cyclohexyl group; a phenyl group; a benzyl group; an alkoxy group having from 1 to 10 carbon atoms, such as a methoxy group, an ethoxy group, a propoxy group and a butoxy group, which may be linear or branched; an aryloxy group, such as a phenoxy group; a hydroxyl group; a cyano group; an amide group; an amino group; and a halogen atom, such as a chlorine atom, a fluorine atom and a bromine atom.

Specific examples of the heterocyclic aromatic amine include 2-(aminomethyl)pyridine, 3-(aminomethyl)pyridine, 4-(aminomethyl)pyridine, 2,3-bis(aminomethyl)pyridine, 2,4-bis(aminomethyl)pyridine, 3,4-bis(aminomethyl)pyridine, 2,5-bis(aminomethyl)pyridine, 2,6-bis(aminomethyl) pyridine, 2-(aminomethyl)pyrimidine, 4-(aminomethyl)pyrimidine, 5-(aminomethyl)pyrimidine, 2,4-bis(aminomethyl) pyrimidine, 2,5-bis(aminomethyl)pyrimidine, 4,5-bis (aminomethyl)pyrimidine and 4,6-bis(aminomethyl) pyrimidine.

The alcohol is not particularly limited as far as it is a compound having a hydroxyl group, and may be an aliphatic alcohol or an aromatic alcohol, and an alcohol having a linear or branched alkyl group having from 1 to 11 carbon atoms, a cycloalkyl group having from 3 to 8 carbon atoms, or an alkyl group having from 1 to 3 carbon atoms having a phenyl group substituted thereon, having a hydroxyl group bonded thereto, and the like may be used. Examples thereof include an alcohol having from 1 to 11 carbon atoms, for example, a primary alcohol, such as methanol, ethanol, 1-propanol, 1-butanol, 1-pentyl alcohol, 1-hexyl alcohol, 1-heptyl alcohol, 1-octyl alcohol, 1-nonyl alcohol, 1-decyl alcohol and 1-undecyl alcohol; a secondary alcohol, such as 2-propanol and 2-butanol; a tertiary alcohol, such as tert-butanol; a cyclic alcohol, such as cyclohexanol; and a polyhydric alcohol, such as ethylene glycol, propylene glycol, diethylene glycol and glycerin. Examples of the aromatic alcohol include benzyl alcohol, 2-phenylethyl alcohol and o-, m- and p-xylene glycol. Among these, an aliphatic alcohol having from 1 to 6 carbon atoms is preferred, and methanol, ethanol, 1-propanol and 1-hexanol are particularly preferred. The alcohols may be used solely or as a combination of two or more kinds thereof. An alkylamine formed along with the aromatic alcohol or the heterocyclic aromatic alcohol is a useful compound, and therefore it is economically advantageous if the alcohol to be reacted is appropriately selected to produce a corresponding alkylamine.

The molar ratio of the alcohol with respect to the raw material amine in the production process of the present invention is preferably from 1 to 1,000, more preferably from 3 to 100, and further preferably from 5 to 30. When the molar ratio of the alcohol is less than 1, the reaction may be prevented from being completed. A molar ratio exceeding 1,000 may be economically disadvantageous.

The basic catalyst used in the production process of the present invention is not particularly limited, and is preferably an alkali metal, such as sodium, potassium and lithium, and a compound thereof, and more preferably metallic sodium, metallic potassium, a sodium compound and a potassium compound. The compound of an alkali metal is preferably a hydroxide and an alkoxide, and particularly preferably sodium hydroxide (NaOH), sodium methoxide ($NaOCH_3$) and potassium hydroxide (KOH). The catalyst may be used solely or as a combination of two or more kinds thereof. The molar ratio of the basic catalyst with respect to the raw material amine in the production process of the present invention is preferably from 0.001 to 100, more preferably from 0.005 to 10, and further preferably from 0.01 to 5. When the molar ratio is less than 0.001, the reaction may be prevented from being completed. A molar ratio exceeding 100 may be economically disadvantageous since by-products tend to be formed.

In the production process of the present invention, water is preferably added to the reaction system. It is considered that the addition of water suppresses the side reaction that proceeds with dehydration reaction, thereby enhancing the selectivity, and enhances the reaction rate itself. Water may be added in an amount of preferably from 0.001 to 2,000, more preferably from 0.05 to 1,000, and further preferably from 0.1 to 500, in terms of molar ratio with respect to the raw material amine. When the molar ratio of water added is less than 0.001, the aforementioned advantages tend to be diminished, and when it exceeds 2,000, the reaction may be prevented from proceeding.

In the production process of the present invention, ammonia is preferably added to the reaction system. It is considered that the addition of ammonia accelerates the reaction. The molar ratio of ammonia used in this case with respect to the raw material amine is preferably from 0.01 to 1,000, more preferably from 0.05 to 100, and further preferably from 0.1 to 50. When the molar ratio is less than 0.01, the aforementioned advantages of amine tend to be diminished. A molar ratio exceeding 1,000 may be economically disadvantageous.

A solvent may not be necessarily used, and an organic solvent may be used, such as benzene, toluene, xylene, nitromethane, nitrobenzene, carbon disulfide, acetonitrile, benzonitrile, hexane, cyclohexane, petroleum ether, diethyl ether, 1,4-dioxane, methyl acetate, tetrahydrofuran, acetone, methyl ethyl ketone, dichloroethane, dimethylformamide, dimethylsulfoxide, dimethyl carbonate and propylene carbonate. These solvents may be used solely or as a combination of two or more kinds thereof.

The production process of the present invention may be performed by any method, for example, by a batch method or a continuous method. Reactive distillation may also be performed, and thereby an alkylamine, which is formed along with the aromatic alcohol or the heterocyclic aromatic alcohol, may be extracted. On performing the batch method, the order of addition of the raw materials may be arbitrarily selected.

The aromatic alcohol or the heterocyclic aromatic alcohol may be isolated from the reaction solution by an ordinary method, such as distillation, recrystallization and extraction. In the production process of the present invention, as described above, an alkylamine is formed along with the aromatic alcohol or the heterocyclic aromatic alcohol. The use of an aliphatic alcohol may provide a secondary or tertiary amine formed by substituting the hydroxyl group of the alcohol by an amino group. Such conditions may be selected that can produce a useful alkylamine efficiently.

The production process of the present invention may be performed under normal pressure, increased pressure or reduced pressure. In the case where the production process of the present invention is performed above the boiling point of the alcohol, the reaction may be performed under the vapor pressure of the alcohol. On performing the reaction under increased pressure, a gas (e.g., nitrogen or argon) that is inert to the production process of the present invention or hydrogen may be used. For example, in the case where an alcohol having a high boiling point is used, reactive distillation may be performed under normal pressure or reduced pressure.

The temperature that is suitable for performing the production process of the present invention depends on the ratio of the raw materials, the reaction conditions and the like, and is, for example, from 50 to 500° C., preferably from 100 to 450° C., and more preferably from 150 to 400° C.

The reaction time depends on the ratio of the raw materials, the reaction conditions and the like, and is preferably from 1 to 1,000 minutes, more preferably from 10 to 500 minutes, and further preferably from 30 to 300 minutes, for the batch method. The reaction time may be optimized in combination with the other conditions.

EXAMPLES

The present invention will be described specifically with reference to examples below, but the present invention is not limited thereto.

The raw materials used were commercially available reagents (produced by Wako Pure Chemical Industries, Ltd. or Tokyo Kasei Kogyo Co., Ltd.), and the resulting reaction solution was analyzed by gas chromatography with the internal reference method. The components therein were identified by comparison in retention time with the commercially available reagents, GC-MASS spectrum and NMR. The conversion ratio and the yield are shown in terms of percent by mol.

Example 1

In a stainless steel pressure resistant vessel having an inner capacity of 40 mL equipped with a thermometer and a manometer, 0.30 g of m-xylylenediamine, 7.50 g of methanol and 0.10 g of sodium hydroxide were charged, and the vessel was sealed under a nitrogen atmosphere. The mixture was heated and held at 240° C. for 2 hours. After cooling, the reaction solution was taken out, and after neutralizing sodium hydroxide, was analyzed. The conversion ratio of m-xylylenediamine was 100%, and the yield of m-xylylene glycol was 73%.

Examples 2 to 5 and Comparative Examples 1 and 2

Investigation of Amines

The reaction was performed in the same manner as in Example 1 except that m-xylylenediamine used in Example 1 was changed to the amines shown in Table 1 below. The results are shown in Table 1 along with Example 1.

TABLE 1

| | Amine | Conversion ratio of raw material (%) | Alcohol formed | Yield (%) |
|---|---|---|---|---|
| Example 1 | m-xylylenediamine | 100 | m-xylylene glycol | 73 |
| Example 2 | p-xylylenediamine | 100 | p-xylylene glycol | 4 |
| Example 3 | benzylamine | 97 | benzyl alcohol | 87 |
| Example 4 | 1,3,5-tri(aminomethyl)benzene | 98 | 1,3,5-benzenetrimethanol | 43 |
| Example 5 | 1-naphthalenemethylamine | 98 | 1-naphthalenemethanol | 78 |
| Comparative Example 1 | 1,3-bis(aminomethyl)cyclohexane | 23 | — | 0 |
| Comparative Example 2 | aniline | 8.9 | — | 0 |

Examples 6 to 25

In a stainless steel pressure resistant vessel having an inner capacity of 40 mL equipped with a thermometer and a manometer, the amine shown in Table 2 below was charged along with methanol, water and sodium hydroxide at a molar ratio of amine/methanol/water/sodium hydroxide of 1/110/70/1.4, and the vessel was sealed under a nitrogen atmosphere. The mixture was heated and held at 240° C. for 2 hours. After cooling, the reaction solution was taken out, and after neutralizing sodium hydroxide, was analyzed. The results are shown in Table 2.

TABLE 2

| | Amine | Conversion ratio of raw material (%) | Alcohol formed | Yield (%) |
|---|---|---|---|---|
| Example 6 | benzylamine | 100 | benzyl alcohol | 91 |
| Example 7 | N-methylbenzylamine | 16 | benzyl alcohol | 6 |
| Example 8 | dibenzylamine | 6 | benzyl alcohol | 4 |
| Example 9 | N,N-dimethylbenzylamine | 16 | benzyl alcohol | 2 |
| Example 10 | 1-phenylethylamine | 41 | 1-phenylethanol | 23 |
| Example 11 | o-methylbenzylamine | 100 | o-methylbenzyl alcohol | 92 |
| Example 12 | m-methylbenzylamine | 100 | m-methylbenzyl alcohol | 93 |
| Example 13 | p-methylbenzylamine | 100 | p-methylbenzyl alcohol | 96 |
| Example 14 | p-tert-butylbenzylamine | 100 | p-tert-butylbenzyl alcohol | 93 |
| Example 15 | p-methoxybenzylamine | 96 | p-methoxybenzyl alcohol | 32 |

TABLE 2-continued

|  | Amine | Conversion ratio of raw material (%) | Alcohol formed | Yield (%) |
|---|---|---|---|---|
| Example 16 | 4-aminobenzylamine | 89 | 4-aminobenzyl alcohol | 7 |
| Example 17 | o-chlorobenzylamine | 100 | o-chlorobenzyl alcohol | 74 |
| Example 18 | p-chlorobenzylamine | 100 | p-chlorobenzyl alcohol | 35 |
| Example 19 | m-fluorobenzylamine | 100 | m-fluorobenzyl alcohol | 40 |
| Example 20 | p-fluorobenzylamine | 86 | p-fluorobenzyl alcohol | 1 |
| Example 21 | p-xylylenediamine | 100 | p-xylylene glycol | 19 |
| Example 22 | 1-naphthylmethylamine | 98 | 1-naphthalenemethanol | 93 |
| Example 23 | 2-(aminomethyl)pyridine | 100 | 2-pyridinemethanol | 82 |
| Example 24 | 3-(aminomethyl)pyridine | 100 | 3-pyridinemethanol | 99 |
| Example 25 | 4-(aminomethyl)pyridine | 100 | 4-pyridinemethanol | 70 |

Examples 26 to 29

In a stainless steel pressure resistant vessel having an inner capacity of 40 mL equipped with a thermometer and a manometer, the amine shown in Table 3 below was charged along with methanol, water and sodium hydroxide at a molar ratio of amine/methanol/water/sodium hydroxide of 1/55/35/0.7, and the vessel was sealed under a nitrogen atmosphere. The mixture was heated and held at 240° C. for 2 hours. After cooling, the reaction solution was taken out, and after neutralizing sodium hydroxide, was analyzed. The results are shown in Table 3.

TABLE 3

|  | Aromatic amine | Conversion ratio of raw material (%) | Alcohol formed | Yield (%) |
|---|---|---|---|---|
| Example 26 | benzylamine | 100 | benzyl alcohol | 96 |
| Example 27 | o-methoxybenzylamine | 97 | o-methoxybenzyl alcohol | 48 |
| Example 28 | m-methoxybenzylamine | 100 | m-methoxybenzyl alcohol | 65 |
| Example 29 | m-chlorobenzylamine | 100 | m-chlorobenzyl alcohol | 91 |
| Example 30 | 4-(dimethylamino)benzylamine dihydrochloride | 92 | 4-dimethylaminobenzyl alcohol | 12 |
| Example 31 | p-xylylenediamine | 100 | p-xylylene glycol | 22 |

Example 30

In a stainless steel pressure resistant vessel having an inner capacity of 40 mL equipped with a thermometer and a manometer, 4-(dimethylamino)benzylamine dihydrochloride was charged along with methanol, water and sodium hydroxide at a molar ratio of amine/methanol/water/sodium hydroxide of 1/110/70/2.4, and the vessel was sealed under a nitrogen atmosphere. The mixture was heated and held at 240° C. for 2 hours. After cooling, the reaction solution was taken out, and after neutralizing sodium hydroxide, was analyzed. The results are shown in Table 3.

Example 31

In a stainless steel pressure resistant vessel having an inner capacity of 40 mL equipped with a thermometer and a manometer, p-xylenediamine was charged along with methanol, water and sodium hydroxide at a molar ratio of amine/methanol/water/sodium hydroxide of 1/110/70/2.8, and the vessel was sealed under a nitrogen atmosphere. The mixture was heated and held at 240° C. for 2 hours. After cooling, the reaction solution was taken out, and after neutralizing sodium hydroxide, was analyzed. The results are shown in Table 3.

Examples 32 to 38

Investigation of Alcohols

The reaction was performed in the same manner as in Example 1 except that methanol was changed to the alcohols shown in Table 4 below. The results are shown in Table 4 along with Example 1.

TABLE 4

|  | Aliphatic alcohol | Conversion ratio of m-xylylenediamine (%) | Yield of m-xylene glycol (%) |
|---|---|---|---|
| Example 1 | methanol | 100 | 73 |
| Example 32 | ethanol | 100 | 77 |
| Example 33 | 1-propanol | 100 | 74 |
| Example 34 | 2-propanol | 48 | 0.7 |
| Example 35 | 1-pentyl alcohol | 91 | 37 |
| Example 36 | 1-hexanol | 100 | 68 |
| Example 37 | 1-undecanol | 92 | 38 |
| Example 38 | ethylene glycol | 100 | 17 |

Examples 39 and 40 and Comparative Example 3

Investigation of Basic Catalysts

The reaction was performed in the same manner as in Example 1 except that sodium hydroxide was changed to the alkali metal compounds shown in Table 5 below. The results are shown in Table 5 along with Example 1.

TABLE 5

| | Basic catalyst | Conversion ratio of m-xylenediamine (%) | Yield of m-xylene glycol (%) |
| --- | --- | --- | --- |
| Example 1 | sodium hydroxide | 100 | 73 |
| Example 39 | sodium methoxide | 100 | 74 |
| Example 40 | potassium hydroxide | 71 | 20 |
| Comparative Example 3 | — | 19 | 0 |

Examples 41 to 43

Investigation of Addition of Water

The reaction was performed in the same manner as in Example 1 except that water was added at the ratios shown in Table 6. The results are shown in Table 6 along with Example 1.

TABLE 6

| | Water/m-xylenediamine (mol) | Conversion ratio of m-xylenediamine (%) | Yield of m-xylene glycol (%) |
| --- | --- | --- | --- |
| Example 1 | 0 | 100 | 73 |
| Example 41 | 17 | 100 | 83 |
| Example 42 | 84 | 100 | 93 |
| Example 43 | 209 | 100 | 92 |

It is understood from Table 6 that the yield is improved by the addition of water.

Examples 44 to 46

Investigation of Reaction Pressure

In a stainless steel pressure resistant vessel having an inner capacity of 40 mL equipped with a thermometer and a manometer, raw materials were charged at a molar ratio of m-xylenediamine/methanol/water/sodium hydroxide of 1/110/70/1.4, and the vessel was sealed under a nitrogen atmosphere. For controlling the pressure on reaction, the pressure inside the reaction vessel was increased with nitrogen to the prescribed pressure, and the vessel was sealed. The mixture was heated and the pressure inside the vessel was measured when the temperature reached 240° C. After being held at 240° C. for 1 hour, the mixture was cooled, and then the reaction solution was taken out, and after neutralizing sodium hydroxide, was analyzed. The results are shown in Table 7.

TABLE 7

| | Pressure on reaching 240° C. (MPa) | Conversion ratio of m-xylenediamine (%) | Yield of m-xylene glycol (%) |
| --- | --- | --- | --- |
| Example 44 | 7.0 | 83 | 24 |
| Example 45 | 8.0 | 77 | 15 |
| Example 46 | 10.2 | 68 | 9 |
| Example 47 | atmospheric pressure | 97 | 36 |

Example 47

Investigation of Reaction Pressure

In a glass three-neck flask having an inner capacity of 100 mL equipped with a stirrer, a reflux condenser and a thermometer, 0.93 g of m-xylenediamine, 0.29 g of sodium hydroxide and 20.6 g of 1-undecanol were charged and refluxed by heating to 235° C. After 1 hour, a part of the reaction solution was taken out, and after neutralizing sodium hydroxide, was analyzed. The conversion ratio of m-xylenediamine was 97%, and the yield of m-xylene glycol was 36%. The results are shown in Table 7.

It is understood from Table 7 that the reaction is facilitated under lower pressure, and the reaction proceeds under normal pressure as shown by Example 47. It is understood from the results that pressurization is not necessary in the production process of the present invention.

Examples 48 to 50

Addition of Ammonia

In a stainless steel pressure resistant vessel having an inner capacity of 100 mL equipped with a thermometer and a manometer, raw materials were charged at a molar ratio of m-xylenediamine/methanol/water/sodium hydroxide of 1/110/70/1.0, to which ammonia was further added at the molar ratios shown in Table 8, and the vessel was sealed under a nitrogen atmosphere. The mixture was heated and held at 240° C. for 1 hour. After cooling, the reaction solution was taken out, and after neutralizing sodium hydroxide, was analyzed. The results are shown in Table 8.

TABLE 8

| | Ammonia/m-xylenediamine (molar ratio) | Conversion ratio of m-xylenediamine (%) | Yield of m-xylene glycol (%) |
| --- | --- | --- | --- |
| Example 48 | 0 | 83 | 24 |
| Example 49 | 5.8 | 92 | 29 |
| Example 50 | 10 | 100 | 60 |

It is understood from Table 8 that even if the reaction time is fixed, the reaction is accelerated by adding ammonia, and thereby the conversion ratio and the yield are both enhanced.

INDUSTRIAL APPLICABILITY

An aromatic alcohol and a heterocyclic aromatic alcohol that are obtained by the present invention may be used as a raw material of a medical drug, agrichemicals and the like, or a plasticizer and a paint solvent, and thus are useful in organic synthetic chemistry. In particular, an aromatic polyhydric alcohol and a heterocyclic aromatic polyhydric alcohol are important compounds as a raw material of a polymer substance, such as a synthetic fiber and a synthetic resin, for example, polyester and polyurethane.

The invention claimed is:

1. A process for producing an aromatic alcohol or a heterocyclic aromatic alcohol, the process comprising reacting an aromatic amine or a heterocyclic aromatic amine, comprising at least one substituent —$CHR^1NR^2R^3$, with an alcohol, in the presence of a basic catalyst, wherein $R^1$, $R^2$ and $R^3$ each independently represent hydrogen, an alkyl group having from 1 to 4 carbon atoms, or a benzyl group.

2. The process of claim 1, wherein the aromatic amine or the heterocyclic aromatic amine is selected from the group consisting of a compound represented by:

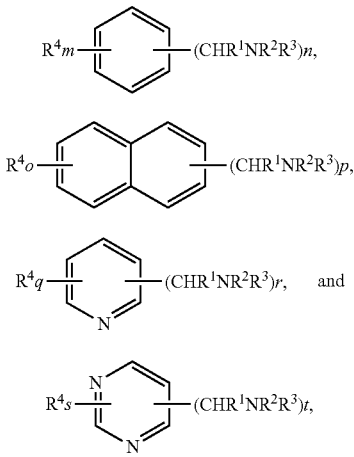

wherein:
$R^1$, $R^2$ and $R^3$ each independently represent hydrogen, an alkyl group having from 1 to 4 carbon atoms, or a benzyl group;
$R^4$ is selected from the group consisting of an alkyl group having from 1 to 10 carbon atoms, a cycloalkyl group having from 3 to 8 carbon atoms, an alkoxy group having from 1 to 10 carbon atoms, a phenyl group, a benzyl group, a hydroxyl group, a cyano group, an amide group, an amino group and a halogen atom;
m represents an integer of from 0 to 5;
n represents an integer of from 1 to 4;
o represents an integer of from 0 to 7;
p represents an integer of from 1 to 4;
q represents an integer of from 0 to 4;
r represents an integer of from 1 to 3;
s represents an integer of from 0 to 3; and
t represents an integer of from 1 to 2,
provided that
m+n is from 1 to 6,
o+p is from 1 to 8,
q+r is from 1 to 5, and
s+t is from 1 to 4.

3. The process of claim 1, wherein the aromatic amine or the heterocyclic aromatic amine is selected from the group consisting of a compound represented by:

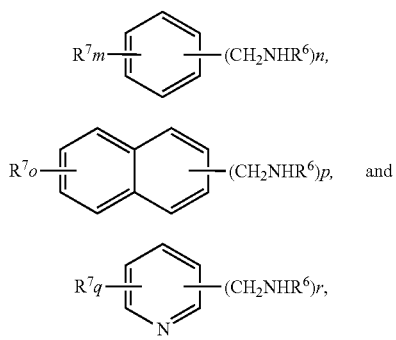

wherein:
$R^6$ represents hydrogen or an alkyl group having from 1 to 4 carbon atoms;
$R^7$ is selected from the group consisting of an alkyl group having from 1 to 10 carbon atoms, a cycloalkyl group having from 3 to 8 carbon atoms, an alkoxy group having from 1 to 10 carbon atoms, a phenyl group, a benzyl group, a hydroxyl group, a cyano group, an amide group and a halogen atom;
m represents an integer of from 0 to 5;
n represents an integer of from 1 to 4;
o represents an integer of from 0 to 7;
p represents an integer of from 1 to 4;
q represents an integer of from 0 to 4; and
r represents an integer of from 1 to 3,
provided that
m+n is from 1 to 6,
o+p is from 1 to 8, and
q+r is from 1 to 5.

4. The process of claim 1, wherein the basic catalyst is at least one selected from the group consisting of metallic sodium, metallic potassium, a sodium compound and a potassium compound.

5. The process of claim 1, wherein the alcohol is an alcohol having a linear or branched alkyl group having from 1 to 11 carbon atoms, a cycloalkyl group having from 3 to 8 carbon atoms, or an alkyl group having from 1 to 3 carbon atoms having a phenyl group substituted thereon, having a hydroxyl group bonded thereto.

6. The process of claim 1, wherein water is added to the reaction.

7. The process of claim 1, wherein ammonia is added to the reaction.

8. The process of claim 2, wherein the basic catalyst is at least one selected from the group consisting of metallic sodium, metallic potassium, a sodium compound and a potassium compound.

9. The process of claim 2, wherein the alcohol is an alcohol having a linear or branched alkyl group having from 1 to 11 carbon atoms, a cycloalkyl group having from 3 to 8 carbon atoms, or an alkyl group having from 1 to 3 carbon atoms having a phenyl group substituted thereon, having a hydroxyl group bonded thereto.

10. The process of claim 2, wherein water is added to the reaction.

11. The process of claim 2, wherein ammonia is added to the reaction.

12. The process of claim 3, wherein the basic catalyst is at least one selected from the group consisting of metallic sodium, metallic potassium, a sodium compound and a potassium compound.

13. The process of claim 3, wherein the alcohol is an alcohol having a linear or branched alkyl group having from 1 to 11 carbon atoms, a cycloalkyl group having from 3 to 8 carbon atoms, or an alkyl group having from 1 to 3 carbon atoms having a phenyl group substituted thereon, having a hydroxyl group bonded thereto.

14. The process of claim 3, wherein water is added to the reaction.

15. The process of claim 3, wherein ammonia is added to the reaction.

* * * * *